US012605540B2

(12) United States Patent
Bricot

(10) Patent No.: US 12,605,540 B2
(45) Date of Patent: Apr. 21, 2026

(54) ENERGY STIMULATION DEVICE PROVIDED WITH A STIMULATION TRANSMITTER

(71) Applicant: Bernard Bricot, Bandol (FR)

(72) Inventor: Bernard Bricot, Bandol (FR)

( * ) Notice: Subject to any disclaimer, the term of this patent is extended or adjusted under 35 U.S.C. 154(b) by 1247 days.

(21) Appl. No.: 17/275,904

(22) PCT Filed: Sep. 10, 2019

(86) PCT No.: PCT/FR2019/052083
§ 371 (c)(1),
(2) Date: Mar. 1, 2022

(87) PCT Pub. No.: WO2020/058599
PCT Pub. Date: Mar. 26, 2020

(65) Prior Publication Data
US 2022/0184388 A1    Jun. 16, 2022

(30) Foreign Application Priority Data
Sep. 20, 2018    (FR) ...................................... 1858528

(51) Int. Cl.
A61N 1/30        (2006.01)
A61N 1/16        (2006.01)
(Continued)

(52) U.S. Cl.
CPC ............... A61N 1/303 (2013.01); A61N 1/16 (2013.01); A61N 1/205 (2013.01); A61N 1/24 (2013.01)

(58) Field of Classification Search
None
See application file for complete search history.

(56) References Cited

U.S. PATENT DOCUMENTS 4,616,654 A  *  10/1986  Bacchelli ............. A61N 1/0456
                                                      607/149
5,284,272 A  *   2/1994  Wei ........................ B65D 23/00
                                                      601/134
(Continued)

FOREIGN PATENT DOCUMENTS

EP          0145673 A1    6/1985
EP          1218058 A1    7/2002
(Continued)

OTHER PUBLICATIONS

Translation of the International Search Report for corresponding PCT/FR2019/052083, dated Dec. 11, 2019.
(Continued)

*Primary Examiner* — Mallika D Fairchild
(74) *Attorney, Agent, or Firm* — Egbert, McDaniel & Swartz, PLLC

(57)        ABSTRACT
An energy stimulation device having at least one stimulation generator provided with at least one first metal body and at least one the second metal body in contact with the first metal body. The first metal body and the second metal body are different metals. The device also includes at least one stimulation transmitter, the stimulation transmitter having a rigid support separate from the stimulation generator, and the stimulation generator being fixed on the rigid support. The energy stimulation device is applicable to bio-stimulation for therapeutic and non-therapeutic purposes.

11 Claims, 3 Drawing Sheets

(51) Int. Cl.
  *A61N 1/20*    (2006.01)
  *A61N 1/24*    (2006.01)

(56)      References Cited

U.S. PATENT DOCUMENTS 6,277,142 B1 *  8/2001  Pinter ................... A61H 39/00
                                                            607/1
6,461,375 B1 *  10/2002  Baudry ................... A61N 1/16
                                                            607/1
6,773,391 B1 *  8/2004  Bricot ..................... A61N 1/24
                                                            600/15

FOREIGN PATENT DOCUMENTS

FR        2642654  A1   8/1990
FR         287917  A1 *  2/2006  .............. A61N 1/16
FR        2873917  A1   2/2006
GB        2154140  A    9/1985

OTHER PUBLICATIONS

Written Opinion of the International Searching Authority for cor-
responding PCT/FR2019/052083 dated Dec. 11, 2019.

* cited by examiner

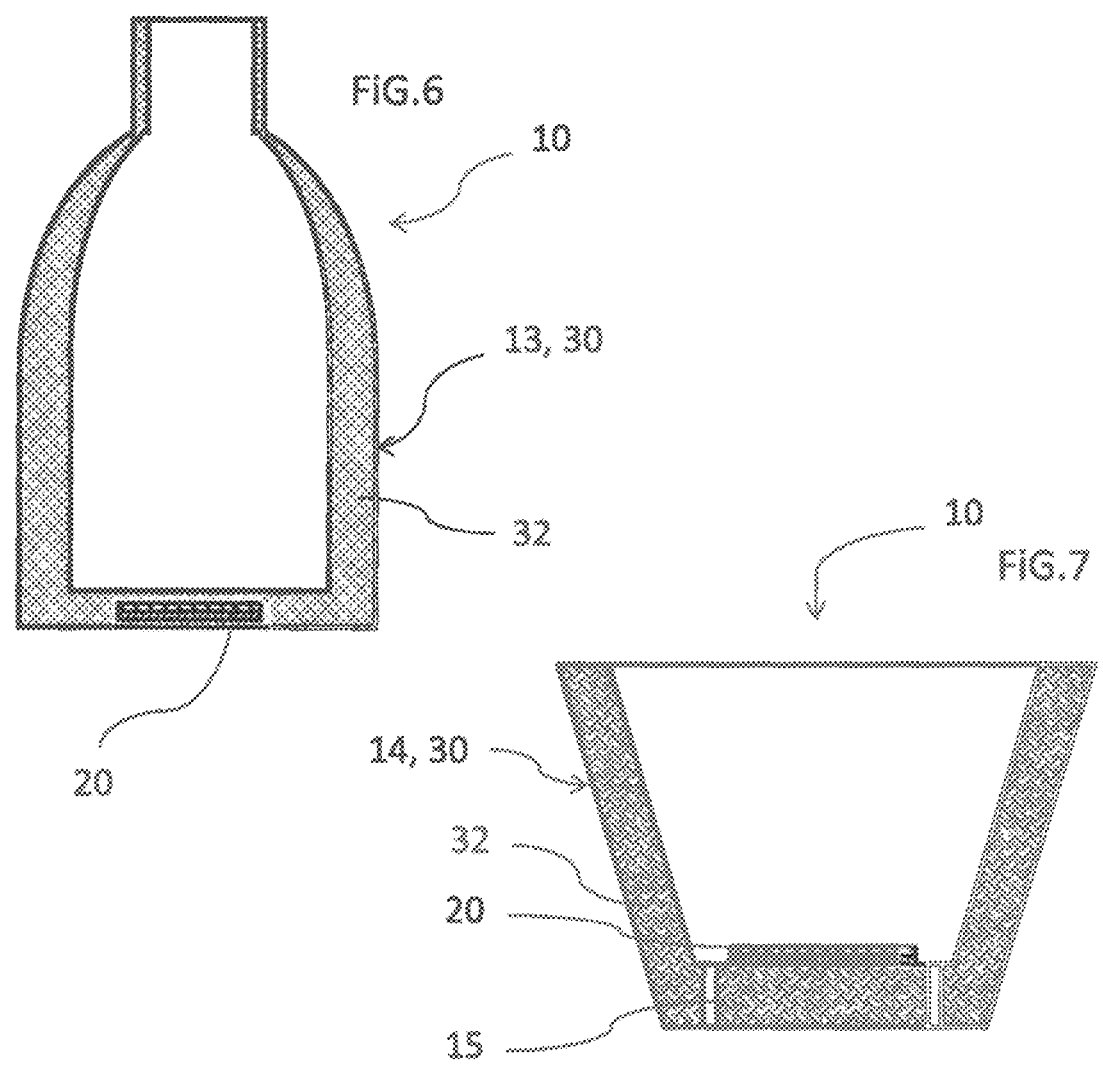
FIG.6
10
13, 30
32
20
14, 30
32
20
15
FIG.7
10
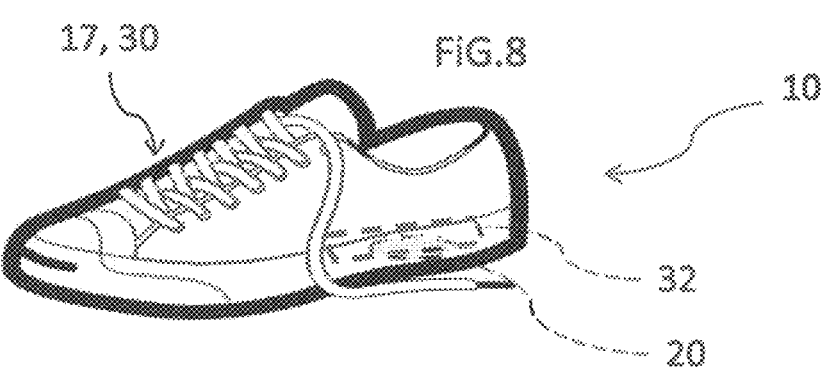
17, 30
FIG.8
10
32
20

ENERGY STIMULATION DEVICE PROVIDED WITH A STIMULATION TRANSMITTER

FIELD OF THE INVENTION

The present invention relates to an energetic stimulation device.

The term energetic used in the remainder of the text is understood in the specific meaning thereof in the fields of energetic medicine, acupuncture or energetic practices applied to the human body or to plants.

The invention has therapeutic applications in particular for the treatment of postural disorders and pathologies, or of symptoms directly or indirectly resulting from a postural disorder.

Further, the device is used as biostimulation instrument for the treatment of pains resulting from a postural disorder or not. It can thus also be used to treat spinal pain, neck pain, lower back pain, back pain but also muscle tears, sprains or "trigger point" type painful points. The device can also be implemented for the treatment of static disorders, such as scoliosis, kyphosis or pelvic tilts. It can also be used for the specific treatment of headaches, neuralgia, scapulalgia and myalgia.

Independent of the medical or therapeutic field, the invention also has applications for enhancing the growth or maturing of plants and fruits, and in particular in the vitiviniculture field for vine growth, wine growing, and storage of wine.

More generally, the invention has applications for human or animal biostimulation and also for biostimulation and the agricultural or agri-food field.

DESCRIPTION OF RELATED ART

The invention constitutes an improvement of a known stimulation device described, for example, in the following patents:

EP 1,218,058, FR 2,798,843 and U.S. Pat. No. 6,773,391. Such a device is also designated by electro-galvanic field device.

Essentially, the device comprises a stimulation generator or stimulation source in the form of a flat plate comprising two different metals in mutual contact and forming a galvanic pair.

The generator can be used as such or be incorporated into clothing, compression support, or sole to keep it near a part of the body that is painful or being treated.

BRIEF SUMMARY OF THE INVENTION

The invention results from a search for improvement of the performance of a known stimulation generator and a search for diversification of the applications thereof.

A goal of the invention is in particular to propose an improved stimulation device, which is more ergonomic and more effective in biostimulation of human and animal bodies.

Another goal of the invention is to make the use of a biostimulation device for therapeutic purposes easier while freeing the user from the constraint of wearing a specific garment, soles or any other accessory holding the device.

A goal of the invention is also to propose a stimulation device suited for non-medical or non-therapeutic applications, for example for vegetable growth or for wine production and storage.

To reach these goals, the invention proposes an energetic stimulation device comprising at least one stimulation generator provided with at least one first metal body and at least one second metal body in electrical and mechanical contact with the first metal body, where the first metal body and the second metal body comprise different metals.

According to the invention, the device further comprises at least one stimulation transmitter, where the stimulation transmitter comprises a rigid support distinct from the stimulation generator, and where the stimulation generator is fixed on the rigid support.

It is considered that the first metal body is in mechanical contact with the second metal body when they touch each other. It is a matter of direct mechanical contact.

It is considered that the stimulation generator is fixed on the rigid support when it is rigidly secured to the rigid support.

The stimulation generator is used as stimulation source. It is comparable to a frequency resonator on the basis of energetic charge and discharge cycles.

It is considered that the first metal body and the second metal body of the stimulation generator comprise different metals when they are made in different metals, meaning different atomic number, but also when they are made from different metal alloys.

In other words, the first metal body and the second metal body form a galvanic pair.

Preferably metals having very different electrochemical potentials can be used so as to form a galvanic pair with a large potential difference.

It is however appropriate to note that metals with very different potentials can be subject to a phenomenon of galvanic corrosion because of their coming into contact. This phenomenon may lead to a draining of the stimulation generator and a reduction of the effects of the stimulation device over time. As needed, a replacement of the stimulation generator can be done.

Advantageously, the first metal body can be made of copper and the second metal body can be made of zinc, so as to join good effectiveness with a good durability of the stimulation device.

The stimulation generator may comprise one or several galvanic pairs, meaning one or several first metal bodies combined with one or several second metal bodies. The reference in the singular to the first metal body and the second metal body thus does not prejudge the number of galvanic pairs constituting the stimulation generator.

Preferably, the stimulation generator may have the shape of a flat plate with one substantially flat main side turned towards the rigid support. Placing the stimulation generator and the rigid support of the stimulation transmitter in contact by the main side serves to guarantee a good energetic coupling. The attachment can be done simply by adhering, by crimping, or by complementary shapes, for example.

It is considered that the main side is a larger area side. When the stimulation generator has the shape of a disk, it may have two opposite sides that are identical or at least the same surface area. In this case, one of the sides is considered as the main side and is turned towards the rigid support.

The stimulation generator is preferably attached onto this rigid support via the side thereof turned towards the rigid support. For example, the main side turned towards the rigid support may be adhered to the rigid support.

According to still other possibilities, the stimulation generator can be crimped in the rigid support or immersed in the material of the rigid support.

Relating to the conformation of the stimulation generator, reference can be made to the document FR 2,798,843, for example. According to a possible embodiment, the first metal body and the second metal body can be superposed disks, having the main sides in contact. The electrical and galvanic contact can be optimized by bringing the main sides, meaning the sides with the largest area, into contact. According to another possibility, the first metal body and the second metal body can also be concentric.

In general, the first metal body and the second metal body are positioned so as to be in mutual electrical contact in order to form a galvanic pair.

The combination of the stimulation generator with a stimulation transmitter, and in particular a stimulation transmitter comprising a rigid support, serves to improve the stimulation effect by activating the transmitter. The improvement may prove to be fairly distinct in a configuration where the device from the invention is configured in the form of a handheld stimulation applicator.

It is considered that the stimulation transmitter comprises a rigid support when all or part of the transmitter is rigid. In particular the stimulation transmitter may comprise the rigid support, rigidly secured with the stimulation generator, and also a nonrigid part. The nonrigid part may be flexible or soft, solid or liquid, or in gel form.

For illustration, the nonrigid part may be a cushion or floormat in which the rigid support and the stimulation generator are incorporated.

It is considered that the support is "rigid" when it is not possible to visibly bend the support without a tool and by human force alone. The rigid character of said rigid support can be conferred on it by the choice of material but also by a choice of dimensions and in particular the thickness.

In particular, the rigid support for the stimulation transmitter can be made of a material chosen from glass, stone, wood, a mineral and a ceramic. Other rigid materials such as a composite material or a resin can also be chosen.

In a particularly advantageous embodiment of the device, the transmitter can be a rock crystal, where the rock crystal constitutes the rigid support. The use of a rock crystal as stimulation transmitter makes it possible to get particularly effective stimulation, particularly in the axis of the crystal, meaning along an axis parallel to the natural lateral facets of the rock crystal. A stimulation of the pulse may be obtained several meters from the axis of the crystal.

According to another possibility, the rigid support, forming the stimulation transmitter, may be a polished stone of the type used in lithotherapy.

More generally, the rigid support may preferably be an electrically insulating material.

Further, the rigid support may preferably have dimensions and/or a mass greater than that of the stimulation generator.

As an example, for a stimulation device in the form of a manual applicator can have one or more stimulation generators, respectively in the form of a disk 1 to 5 cm in diameter and a thickness of order one or a few millimeters. The rigid support, for example a rock crystal, may have a length of 10 to 20 cm and a diameter of 4 to 5 cm, or even more.

The stimulation transmitter may have a shape suited to the use and destination of the stimulation device.

For example, for a use of the device as a manual applicator, the transmitter may have at least one from a part having a flat and polished side, and a part forming a point.

A polished side may be beneficially used to massage an area of the body needing to be stimulated. In contrast, a part forming the point makes the transmission of the stimulation more effective towards acupuncture points, acupressure points, chakras or simply towards painful areas.

One or several applications of the simulation device on the parts of the body to be treated or on the painful parts, respectively during a period of a few minutes, serves to provide postural corrections.

Other configurations of the stimulation device, and the stimulation transmitter, are conceivable.

The stimulation transmitters may in particular be configured in the shape of one of the following articles:

a food container;

a seat;

a part of a seat;

a part of a bed;

a cushion;

a mat;

a prosthesis;

a shoe;

a culture container.

In the case of the shoe, a rigid support for the stimulation transmitter may make up, for example, a shoe heel.

In the case of a prosthesis, the rigid support may make up, for example, a reinforcement of the prosthesis.

A seat, for example a chair or armchair, or a seat part, a seatback or seat bottom, may also make up the stimulation transmitter for biostimulation sessions in seated position. It is the same for a bed, or bed part, for biostimulation in stretched-out position.

The stimulation device in the form of a chair or an armchair serves to renew a stimulation each time that the user sits on the chair and thus makes it possible to get an extended treatment.

In the case of a cushion or a mat, the rigid support and the stimulation generator can be incorporated in a part that does not compromise the comfort in use.

The stimulation transmitter may also be a food container and in particular a bottle.

The use of a stimulation transmitter in the form of a food container and or a bottle serves, for example, a use for better storage and/or better aging of wine.

Finally, the stimulation transmitter may come in the form of a culture container, for example a planter or more simply a flowerpot.

A culture container is understood to mean a container which could receive a substrate for culturing plants, animal cells or vegetable cells. The culture substrate may be considered as making up part of the transmitter, for which the rigid part is, further, made up by a wall of the culture container.

The device from the invention in the form of a culture container serves in particular to stimulate the germination and growth of green plants, vegetable plants and ornamental plants. In this case, it is a matter of plants grown in a culture substrate received in the culture container.

Other characteristics and advantages of the invention emerge from the following description, with references to the figures from the drawings. This description is given purely for illustration and is nonlimiting.

BRIEF DESCRIPTION OF THE DRAWINGS

FIG. 6 is a schematic section along a plane of symmetry of a stimulation device conforming to the invention configured in the form of a food container, and in particular a bottle.

FIG. 7 is a schematic section along the plane of symmetry of a stimulation device conforming to the invention configured in the form of a culture container.

FIG. 8 is a schematic representation of a stimulation device conforming to the invention configured in the form of a shoe.

The figures are not executed to scale.

DETAILED DESCRIPTION OF THE INVENTION

In the following description, identical, similar or equivalent parts from different figures are indicated with the same reference marks to improve the transfer from one figure to another.

Figure 1:
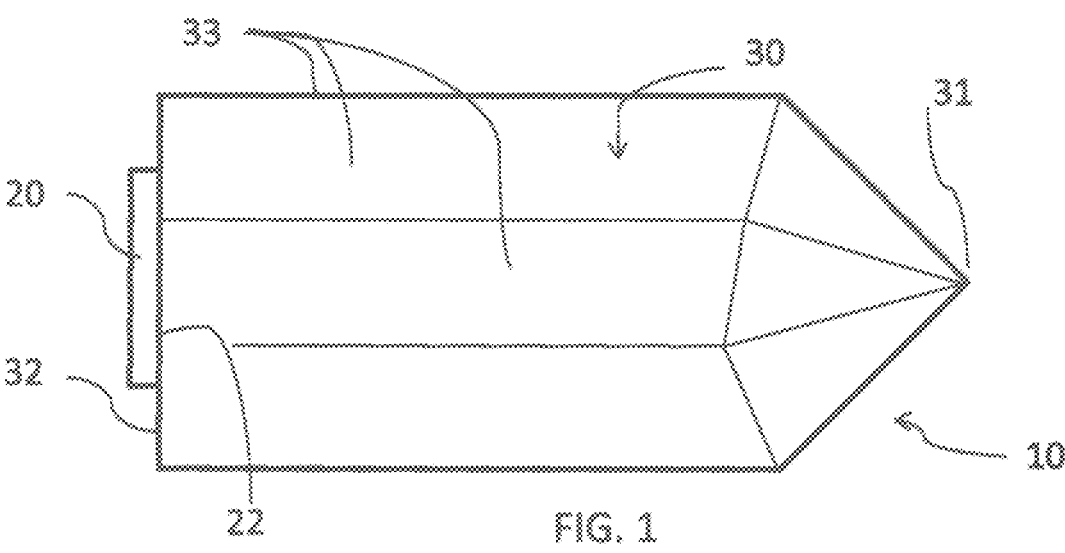
FIG. 1 is a schematic representation of a stimulation device conforming to the invention.

FIG. 1 shows a stimulation device 10 conforming to the invention comprising a stimulation generator 20, or source, and a stimulation transmitter 30.

The stimulation generator 20 has the shape of a flat bimetallic disk. It has a flat main side 12, in contact with the stimulation transmitter 30.

The stimulation transmitter 30 is a block of rock crystal. It has a front end forming a point 31, flat and smooth lateral sides 33, and a flat rear end which constitutes a rigid support 32 receiving the stimulation generator 20.

The rear side 22 of the stimulation generator is held rigidly on the rigid support 32, for example, by adhering or by crimping.

A stimulation device comparable to the one from FIG. 1 can be used, for example, by applying the stimulation transmitter 30 against the body or against clothing of a patient in a painful area. According to another possibility, the point 31 of the stimulation transmitter 30 can be oriented towards an acupuncture point and/or be brought into contact with the acupuncture point.

The dimensions of the stimulation transmitter may be variable according to the rock crystal block used. They are preferably suited to being taken in hand easily. More economic models of a stimulation device conforming to FIG. 1 can be done by replacing the rock crystal with a glass block or polished stone, for example.

Figure 2:
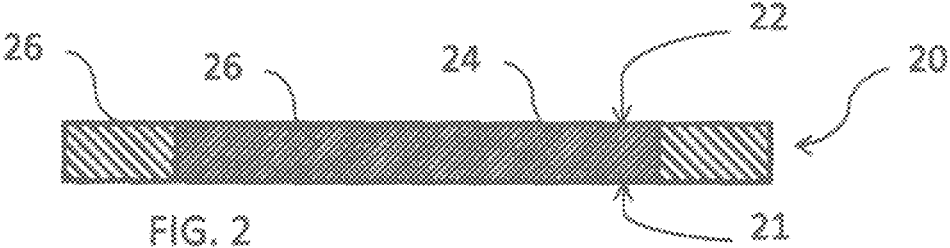
FIG. 2 is a schematic section of a stimulation generator that can be used in a stimulation device conforming to the invention.

FIG. 2 shows in section an implementation possibility of the stimulation generator 20 from FIG. 1.

In this embodiment, the stimulation generator is formed by concentric crimping of two metal bodies 24, 26. A first metal body 24, for example copper, has the shape of a disk. A second metal body 26, for example of zinc, has the shape of a ring receiving, in its center, the disk of the first metal body. The two metal bodies have the same thickness so as to give them flat main sides 21, 22. When the stimulation generator 20 from FIG. 2 is combined with the stimulation transmitter, one of the main sides 21, 22 is applied onto the rigid support of the transmitter. It may in particular be adhered.

FIG. 3 again shows another implementation possibility in which the stimulation generator is made up of two metal disks 24, 26 in mutual mechanical and electrical contact by the main sides. The two disks are, for example, a copper disk and a zinc disk or a brass disk and a steel disk.

The metal disks can be fixed one on the other by crimping or by nesting, for example.

Figure 3:
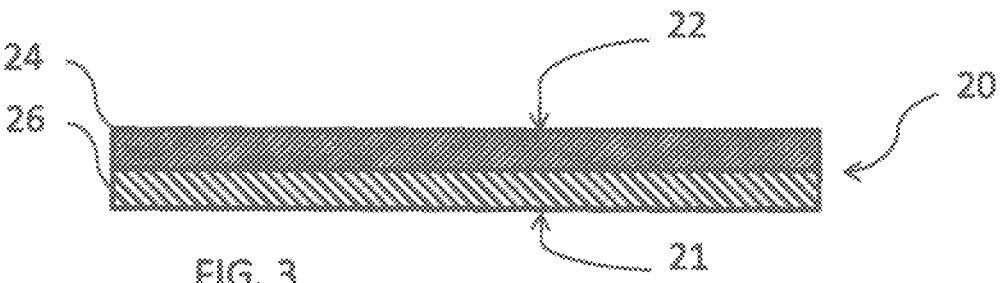
FIG. 3 is a schematic section of another stimulation generator that can be used in the stimulation device conforming to the invention.

When the stimulation generator 20 from FIG. 3 is combined with a stimulation transmitter, one of the disks is applied onto the rigid support of the transmitter by the main free side 21, 22 thereof.

Figure 4:
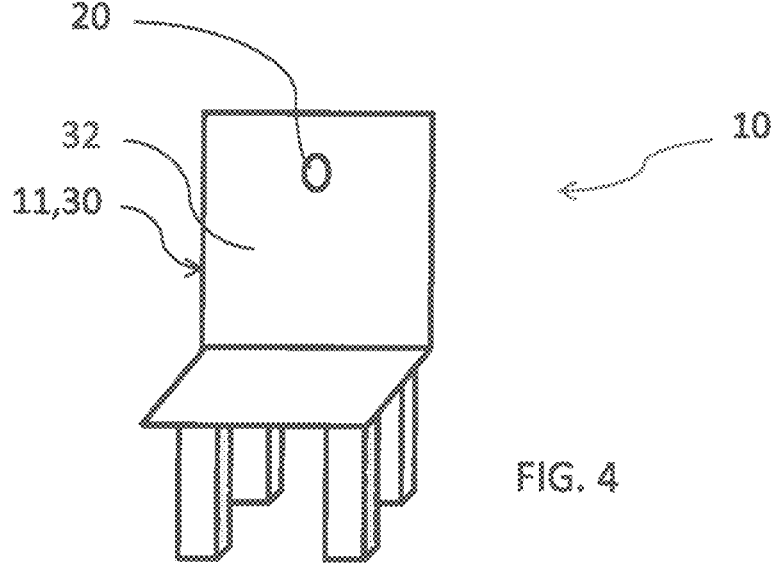
FIG. 4 is a schematic representation of a stimulation device conforming to the invention configured in the form of a seat.

FIG. 4 shows an implementation of the invention in which the stimulation device 10 and in particular the stimulation transmitter 30 is a seat 11.

More specifically it involves a chair whose seatback makes up the rigid support 32 of the stimulation transmitter. The seatback is for example made of wood or a composite material. It receives the stimulation generator 20. The generator may simply be adhered against the seat back, embedded in the material making up the seatback or crimped in a housing prepared in the seatback.

FIG. 5 again shows another possibility for implementation of the device from the invention 10 in the form of a floormat 12.

For the most part, the floormat 12 has the shape of a flexible, foam plate that makes up the stimulation transmitter 30. The floormat also comprises a part 36 that forms a cushion and also makes up a stimulation transmitter.

Conforming to the invention, the transmitter assembly is not flexible. In fact, the rigid plates 34, for example, the rigid plastic plates, are applied against the foam plate or embedded in the foam plate. They make up respectively rigid supports 32 in the meaning of the invention and each receives the stimulation generator 20.

The stimulation generators and the rigid supports are not visible on the upper side of the mat 12 and are thus shown in broken lines.

Figure 5:
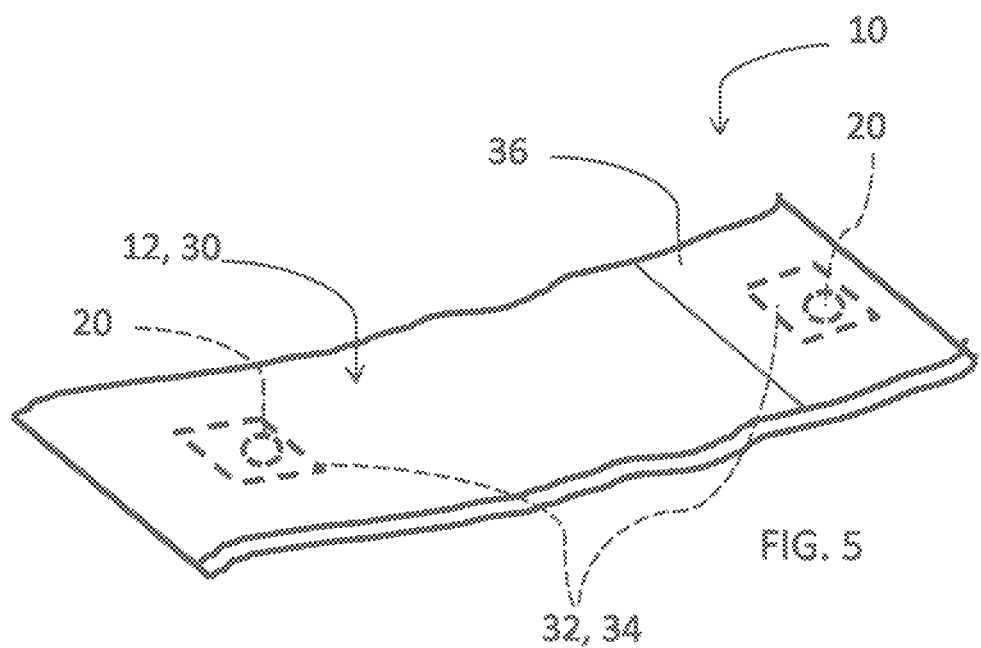
FIG. 5 is a schematic representation of a stimulation device conforming to the invention configured in the form of a cushion or a floormat.

In the example from FIG. 5, two stimulation generators 20 are shown. They are respectively associated with two rigid supports 32, 34. In this respect it is appropriate to indicate that a larger number of stimulation generators and a larger number of rigid supports may be implemented. Likewise, each rigid support may bear several stimulation generators.

A bed, a part of a bed, a mattress, or a cushion may be configured analogously to that of the mat from FIG. 5.

FIG. 6 shows a possibility for implementation of the invention in which the stimulation device 10, and more precisely the stimulation transmitter 30, is a food container. It involves more precisely a bottle 13. It is shown in section.

The wall of the bottle 13 is a rigid wall, made, for example, of glass, and constitutes a rigid support 32 in the meaning of the invention and also the stimulation transmitter 30. The stimulation generator 20 has the shape of a bimetal disk adhered against the wall of the bottle or embedded in the wall of the bottle 13. The stimulation generator may, for example, have a place in the bottom of the bottle.

Such a bottle may be implemented to improve wine storage and aging. Similarly, one or more stimulation generators may be applied on the wall of a vat or hogshead to improve the maturing of wine.

FIG. 7 shows in section a culture container 14, such as a planter or a flowerpot which makes up the stimulation transmitter 30 of a stimulation device 10 conforming to the invention.

The wall of the culture container 14, for example of terra-cotta, constitutes the rigid support 32 of the stimulation transmitter.

In fact, a bimetal stimulation generator 20 is adhered against the wall of the culture container.

In the sample implementation shown, the stimulation generator is adhered inside the culture container 14 on the wall forming the bottom.

The generator can also be placed on any other part of the wall, inside or outside, of the culture container 14.

Reference 15 indicates drains made in the bottom of the culture container 14.

FIG. 8 shows an implementation of a stimulation device 10, conforming to the invention in the form of a shoe 17. The shoe, and in particular the heel of the shoe, forms a stimulation transmitter 30.

In this embodiment, the heel comprises a stimulation generator 20 secured as needed to a rigid insert 32 forming the rigid support.

Comparably to FIG. 8, the stimulation device may also make up clothing, orthotics or prostheses.

The invention claimed is:

1. A stimulation device comprising:
at least one stimulation generator having at least one first metal body and at least one second metal body, the at least one second metal body being in electrical and mechanical contact with the at least one first metal body, wherein a metal of the at least one first metal body is different than a metal of the at least one second metal body, wherein the at least one first metal body and the at least one second metal body form a galvanic pair; and
at least one stimulation transmitter having a rigid support distinct from said at least one stimulation generator, said at least one stimulation generator being fixed on the rigid support, the rigid support being inflexible, wherein said at least one stimulation generator has a flat plate shape with a substantially flat main side turned toward the rigid support.

2. The stimulation device of claim 1, wherein the rigid support said at least one stimulation transmitter has an area greater than an area of said at least one stimulation generator.

3. The stimulation device of claim 1, wherein the rigid support is formed of an electrically insulative material.

4. The stimulation device of claim 3, wherein the electrically insulative material is a material selected from the group consisting of a glass, a stone, a wood, a mineral and a ceramic.

5. The stimulation device of claim 1, wherein said at least one stimulation transmitter is a rock crystal, the rock crystal being the rigid support.

6. The stimulation device of claim 1, wherein the at least one first metal body is formed of copper, the at least one second metal body being formed of zinc.

7. The stimulation device of claim 1, wherein the at least one first metal body and the at least one second metal body are superposed disks with respective main sides in contact.

8. The stimulation device of claim 1, wherein the at least one first metal body and the at least one second metal body are concentric to each other.

9. The stimulation device of claim 1, wherein said at least one stimulation transmitter has at least one of a polished flat suitable and a part forming a point.

10. The stimulation device of claim 1, wherein said at least one stimulation transmitter has a shape selected from the group consisting of a food container, a seat, a portion of a seat, a portion of a bed, a prosthesis, a shoe and a culture container.

11. The stimulation device of claim 1, wherein said at least one stimulation transmitter is a bottle.

* * * * *